United States Patent [19]
Wood et al.

[11] Patent Number: 5,883,104
[45] Date of Patent: Mar. 16, 1999

[54] METHODS FOR IMPROVING THE RESIDUAL CONTROL OF MITES AND PROLONGING THE PROTECTION OF PLANTS FROM MITES INFESTATIONS

[75] Inventors: William Wakefield Wood, Pennington; Salvatore John Cuccia, Lawrenceville, both of N.J.; Michael F. Treacy, Newtown, Pa.

[73] Assignee: American Cyanamid Company, Madison, N.J.

[21] Appl. No.: 874,116

[22] Filed: Jun. 12, 1997

[51] Int. Cl.⁶ .................................................. A01N 43/54

[52] U.S. Cl. .............................................. 514/269

[58] Field of Search .............................................. 514/269

[56] References Cited

FOREIGN PATENT DOCUMENTS 9402470 2/1994 WIPO .

*Primary Examiner*—Allen J. Robinson
*Attorney, Agent, or Firm*—Timothy J. Babcock

[57] ABSTRACT

The present invention provides methods for improving the residual control of mites and prolonging the protection of plants from mite infestations by applying to the foliage of plants an unsymmetrical 4,6-bis(aryloxy)pyrimidine compound of formula I

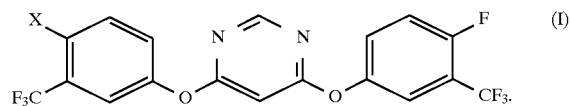

8 Claims, No Drawings

METHODS FOR IMPROVING THE RESIDUAL CONTROL OF MITES AND PROLONGING THE PROTECTION OF PLANTS FROM MITES INFESTATIONS

BACKGROUND OF THE INVENTION

Mites cause tremendous economic losses in horticultural plants and agricultural crops. In particular, mites devastate citrus and pome fruit by feeding on leaves and ripening fruit.

To control mite infestations, plants are treated several times during the growing season with commercial miticides. In spite of multiple applications of the commercial miticides available today, damage to plants caused by mite infestations still occurs. Accordingly, there is ongoing research to discover new and more effective miticidal agents which do not require multiple applications to protect plants from mite infestations.

Certain pyrimidine compounds which are useful as miticidal agents are described in WO 94/02470. However, that publication does not disclose any residual miticidal activity.

It is, therefore, an object of the present invention to provide a method for improving the residual control of mites.

It is also an object of the present invention to provide a method for prolonging the protection of plants from mite infestations.

Those and other objects of the present invention will become more apparent from the detailed description thereof set forth below.

SUMMARY OF THE INVENTION

The present invention provides methods for improving the residual control of mites and prolonging the protection of plants fr6m mite infestations by applying to the foliage of plants susceptible to mite infestation a miticidally effective amount of an unsymmetrical 4,6-bis(aryloxy)pyrimidine compound.

DETAILED DESCRIPTION OF THE INVENTION

The present invention provides a method for improving the residual control of mites which comprises applying to the foliage of a plant susceptible to mite infestation a miticidally effective amount of an unsymmetrical 4,6-bis (aryloxy)pyrimidine compound having the structural formula I

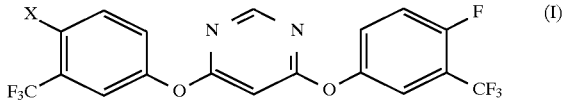

wherein

X is Cl, nitro or cyano.

The present invention also provides a method for prolonging the protection of a plant from mite infestation which comprises applying to the foliage of the plant a miticidally effective amount of an unsymmetrical 4,6-bis(aryloxy) pyrimidine compound of formula I.

The unsymmetrical 4,6-bis(aryloxy)pyrimidine compounds of this invention and the corresponding symmetrical analogues thereof are described in WO 94/02470. That publication only discloses acute (non-residual) miticidal evaluations. Surprisingly, it has now been found that when biologically equivalent acute doses (i.e. $LC_{99}$ values) of pyrimidine compounds are applied to plants, that the unsymmetrical 4,6-bis(aryloxy) pyrimidine compounds of this invention are significantly more effective for the residual control of mites than the corresponding symmetrical pyrimidine analogues.

Advantageously, season-long protection from mite infestations may be achieved by a single application of an unsymmetrical 4,6-bis(aryloxy)pyrimidine compound of this invention. Beneficially, season-long protection from one application of an unsymmetrical 4,6-bis(aryloxy) pyrimidine compound of this invention would significantly reduce the environmental burden associated with the use of conventional miticides which require multiple applications to protect plants from mite infestations.

In a preferred embodiment of the present invention, the unsymmetrical 4,6-bis(aryloxy)pyrimidine compound is 4-[(4-chloro-α,α,α-trifluoro-m-tolyl)oxy]-6-[(α,α,α,4-tetrafluoro-m-tolyl)oxy]pyrimidine.

The formula I compounds of this invention are especially useful for the residual control of herbivorous mites, including but not limited to, Tetranychidae such as *Tetranychus urticae, Tetranychus pacificus, Tetranychus kanzawai, Panonychus ulmi, Panonychus citri* and *Oligonychus pratensis*; Tarsonemidae such as *Phytonemus pallidus* and *Polyphagotarsonemus latus*; Eriophyidae such as *Aculus schlechtendali, Phyllocoptrata oleivora* and *Eriophyes sheldoni*; and Tenuipalpidae such as *Brevipalpus phoenicis*. In particular, the unsymmetrical 4,6-bis(aryloxy)pyrimidine compounds of this invention are especially useful for the residual control of *Tetranychus urticae, Panonychus ulmi, Panonychus citri* and *Brevipalpus phoenicis*.

Plants which are protected from mite infestations for prolonged periods by the formula I compounds of this invention include, but are not limited to, citrus plants such as orange, grapefruit, lemon and lime; pome fruits such as apple, pear and kiwi; stone fruits such as avocado, peach, cherry, fig, olive and mango; vine fruits such as grape, strawberry and raspberry; nut crops such as almond, pecan, walnut, pistachio, cashew, filbert, chestnut, macadamia and Brazil nut; field crops such as cotton, corn, soybean, wheat, squash and watermelon; ornamental plants such as flowering plants and shrubs; coffee; and tea. The unsymmetrical 4,6-bis(aryloxy)-pyrimidine compounds of this invention are especially useful for protecting citrus plants and pome fruits from mite infestations for prolonged periods.

To provide prolonged residual control of mites, orchard and ornamental plants are generally treated with a liquid, preferably aqueous, dispersion which contains about 1 g/hl to 100 g/hl, preferably 5 g/hl to 25 g/hl, of a formula I unsymmetrical 4,6-bis(aryloxy)pyrimidine compound. In practice, the dispersion is generally applied to the orchard or ornamental plant to runoff.

The unsymmetrical 4,6-bis(aryloxy)pyrimidine compounds of this invention are also useful for prolonging the residual control of mites in field crops when applied to the crops in sufficient amount to provide a rate of about 0.01 kg/ha to 1.0 kg/ha, preferably about 0.08 kg/ha to 0.3 kg/ha, of active ingredient.

The term "foliage" as used herein includes, but is not limited to, the leaves, buds, fruit, stems, twigs, branches and/or flowers of plants. The term "orchard plant" as used herein includes, but is not limited to, citrus plants, pome fruits, stone fruits, vine fruits and nut crops. The term "ornamental plant" as used herein includes, but is not limited to, flowering plants and shrubs. And the term "field crop" as used herein includes, but is not limited to, vegetables such as squash and watermelon, and row crops such as cotton, corn, soybean and wheat.

The unsymmetrical 4,6-bis(aryloxy)pyrimidine compounds of this invention may be formulated as emulsifiable concentrates, flowable concentrates or wettable powders which are diluted with water or other suitable polar solvent, generally in situ, and then applied as a dilute spray. The unsymmetrical 4,6-bis(aryloxy)pyrimidines may also be formulated in dry compacted granules, granular formulations, dusts, dust concentrates, suspension concentrates, microemulsions and the like. Such formulations or compositions of the present invention include an unsymmetrical 4,6-bis(aryloxy)pyrimidine compound of this invention (or combinations thereof) admixed with one or more agronomically acceptable inert, solid or liquid carriers.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Evaluation of residual miticidal activity against twospotted spider mites under greenhouse conditions The leaves of sieva lima bean plants are dipped in 50% acetone test solutions. Each test solution contains 2 times the twospotted spider mite $LC_{99}$ value of the compound being evaluated. The $LC_{99}$ value used is that concentration of the compound in ppm which kills 99 percent of twospotted spider mites in an acute dose evaluation. By using the $LC_{99}$ values, biologically equivalent acute doses of the test compounds are provided at the beginning of the evaluation. The plants are then allowed to dry, placed in flats, bottom watered, placed in a greenhouse, and held under light for 14 hours per day. The plants are then subsampled at 0, 3 and 7 days after treatment. At each sampling period, the appropriate plants are removed from the greenhouse and infested with about 50–60 twospotted spider mites per leaf. After three days, adult mite counts are made and mite mortality is estimated. The results are summarized in Table I.

The compounds evaluated are identified below. Data in Table I are reported by compound number for the invention compounds and by compound letter for the comparison compounds.

As can be seen from the data in Table I, the unsymmetrical 4,6-bis(aryloxy)pyrimidine compounds of this invention are surprisingly more effective for the residual control of twospotted spider mites than the corresponding symmetrical analogues. This is an especially unexpected result because biologically equivalent acute doses are initially applied to the plants.

TABLE I

Residual Activity of Pyrimidines

| Compound | Rate 2X-$LC_{99}$ ppm | % Mortality of Twospotted Spider Mites (*Tetranychus urticae*) Days After Treatment | | |
|---|---|---|---|---|
| | | 0 | 3 | 7 |
| Invention Compound 1 | 7 | 100 | 99 | 99 |
| Invention Compound 2 | 10 | 100 | 96 | 97 |
| Symmetrical Compound A | 8 | 100 | 80 | 25 |
| Symmetrical Compound B | 6 | 100 | 49 | no evaluation |

EXAMPLE 2

Field evaluation of residual miticidal activity

The residual control of several herbivorous mite species in tree fruit and citrus is evaluated in the field by applying an aqueous mixture containing 5 or 15 g/hl of the test compound to the foliage of the plants with a hand-held boom at a spray volume of about 1,000 to 2,000 l/ha (i.e.—applied to runoff). The aqueous mixture is prepared by adding the appropriate amount of an emulsifiable concentrate of the test compound to water. In this evaluation, the emulsifiable concentrate contains 9.7 wt/wt % of the test compound, 3.5 wt/wt % of TOXIMUL® 3403F (an anionic/nonionic detergent blend available from Stepan Company, Northfield, Ill.), 3.5 wt/wt % of TOXIMUL® 3404F (an anionic/nonionic detergent blend available from Stepan Company), and 83.3 wt/wt % of AROMATIC® 200 (an aromatic hydrocarbon solvent available from EXXON Chemicals Americas, Houston, Tex.).

Following application, the plants are inspected on about a weekly basis for the presence of live mites. The residual activity of the test compounds is then evaluated by comparing the number of mites on treated vs untreated plants. The results are summarized in Tables II–VI. In Tables II–VI the compounds are identified by the compound number or letter given in Example 1.

| Compound | Structural Formula | Chemical Name |
|---|---|---|
| Invention Compound 1 | (structure) | 4-[(4-Chloro-α,α,α-trifluoro-m-tolyl)oxy]-6-[(α,α,α,4-tetrafluoro-m-tolyl)oxy]pyrimidine |
| Invention Compound 2 | (structure) | 4-[(α,α,α,4-Tetrafluoro-m-tolyl)oxy]-6-[(α,α,α-trifluoro-4-nitro-m-tolyl)oxy]-pyrimidine |
| Symmetrical Compound A | (structure) | 4,6-Bis[(α,α,α-4-tetrafluoro-m-tolyl)oxy]-pyrimidine |
| Symmetrical Compound B | (structure) | 4,6-Bis[(4-chloro-α,α,α-trifluoro-m-tolyl)oxy]pyrimidine |

As can be seen from the data in Tables II–VI, the unsymmetrical 4,6-bis(aryloxy)pyrimidine compound of this invention (4-[(4-chloro-α,α,α-trifluoro-m-tolyl)oxy]-6-[(α,α,α,4-tetrafluoro-m-tolyl)oxy]pyrimidine) provides a significantly greater level of residual control of leprosis mite, red mite and European red mite than the symmetrical pyrimidine analogue (4,6-bis[(α,α,α,4-tetrafluoro-m-tolyl)oxy]pyrimidine).

TABLE II

Evaluation of Field Applications of Pyrimidines Against *Brevipalpus phoenicis* (leprosis mite) on Orange—Evaluation 1

| Treatment | Rate (g/hl) | Percent Mite Control Days After Treatment | | | |
|---|---|---|---|---|---|
| | | 7 | 28 | 50 | 63 |
| Invention Compound 1 | 15 | 94 | 100 | 90 | 100 |
| | 5 | 100 | 100 | 93 | 88 |
| Symmetrical Compound A | 15 | 97 | 100 | 93 | 88 |
| | 5 | 94 | 100 | 69 | 68 |

TABLE III

Evaluation of Field Applications of Pyrimidines Against *Brevipalpus phoenicis* (leprosis mite) on Orange—Evaluation 2

| Treatment | Rate (g/hl) | Percent Mite Control Days After Treatment | | | | |
|---|---|---|---|---|---|---|
| | | 7 | 30 | 70 | 90 | 120 |
| Invention Compound 1 | 15 | 100 | 98 | 98 | 94 | 99 |
| | 5 | 100 | 94 | 96 | 91 | 79 |
| Symmetrical Compound A | 15 | 100 | 94 | 98 | 58 | 63 |
| | 5 | 100 | 95 | 89 | 58 | 64 |

TABLE IV

Evaluation of Field Applications of Pyrimidines Against *Brevipalpus phoenicis* (leprosis mite) on Orange—Evaluation 3

| Treatment | Rate (g/hl) | Percent Mite Control Days After Treatment | | | | |
|---|---|---|---|---|---|---|
| | | 7 | 35 | 60 | 90 | 124 |
| Invention Compound 1 | 15 | 89 | 100 | 100 | 100 | 98 |
| | 5 | 95 | 100 | 98 | 98 | 80 |
| Symmetrical Compound A | 15 | 97 | 100 | 100 | 98 | 71 |
| | 5 | 96 | 94 | 95 | 72 | 0 |

TABLE V

Evaluation of Field Applications of Pyrimidines Against *Panonychus citri* (red mite) on Orange

| Compound | Rate (g/hl) | Percent Mite Control Days After Treatment | | |
|---|---|---|---|---|
| | | 7 | 21 | 30 |
| Invention Compound 1 | 15 | 99 | 97 | 94 |

TABLE V-continued

Evaluation of Field Applications of Pyrimidines Against *Panonychus citri* (red mite) on Orange

| Compound | Rate (g/hl) | Percent Mite Control Days After Treatment | | |
|---|---|---|---|---|
| | | 7 | 21 | 30 |
| Symmetrical Compound A | 15 | 88 | 85 | 69 |

TABLE VI

Evaluation of Field Applications of Pyrimidines Against *Panonychus ulmi* (European red mite) on Apple

| Treatment | Rate (g/hl) | Percent Mite Control Days After Treatment | | | |
|---|---|---|---|---|---|
| | | 2 | 14 | 21 | 36 |
| Invention Compound 1 | 15 | 97 | 99 | 97 | 94 |
| | 5 | 77 | 92 | 94 | 64 |
| Symmetrical Compound A | 15 | 90 | 93 | 96 | 78 |
| | 5 | 77 | 70 | 86 | 28 |

What is claimed is:

1. A method for improving the residual control of mites and prolonging the protection of a plant from mite infestation which comprises applying to the foliage of a plant susceptible to mite infestation a miticidally effective amount of an unsymmetrical 4,6-bis(aryloxy)pyrimidine compound having the structural formula

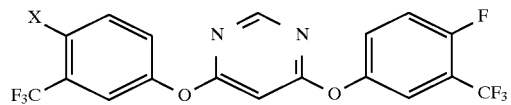

wherein

X is Cl, nitro or cyano.

2. The method according to claim 1 wherein the compound is 4-[(4-chloro-α,α,α-trifluoro-m-tolyl)oxy]-6-[(α,α,α,4-tetrafluoro-m-tolyl)oxy]pyrimidine.

3. The method according to claim 1 wherein the plant is selected from the group consisting of a citrus plant, a pome fruit, a stone fruit, a vine fruit, a nut crop, a field crop, an ornamental plant, coffee and tea.

4. The method according to claim 3 wherein the plant is a citrus plant or a pome fruit.

5. The method according to claim 1 wherein the mites are-selected from the group consisting of *Tetranychus urticae, Tetranychus pacificus, Tetranychus kanzawai, Panonychus ulmi, Panonychus citri, Oligonychus pratensis, Phytonemus pallidus, Polyphagotarsonemus latus, Aculus schlechtendali, Phyllocoptrata oleivora, Eriophyes sheldoni* and *Brevipalpus phoenicis*.

6. The method according to claim 5 wherein the mites are selected from the group consisting of *Tetranychus urticae, Panonychus ulmi, Panonychus citri* and *Brevipalpus phoenicis*.

7. The method according to claim 1 wherein the plant is an orchard or ornamental plant and the compound is applied to the foliage of the plant at a rate of about 1 g/hl to 100 g/hl.

8. The method according to claim 1 wherein the plant is a field crop and the compound is applied to the foliage of the plant at a rate of about 0.01 kg/ha to 1.0 kg/ha.

* * * * *